(12) United States Patent
Sandler et al.

(10) Patent No.: US 10,159,620 B2
(45) Date of Patent: Dec. 25, 2018

(54) GAIT ORTHOTIC SYSTEM AND METHOD FOR ACHIEVING HANDS-FREE STABILITY

(71) Applicant: Ekso Bionics, Inc., Richmond, CA (US)

(72) Inventors: Reuben Sandler, Berkeley, CA (US); Katherine Strausser, Berkeley, CA (US); Adam Zoss, Berkeley, CA (US); Tim Swift, Clovis, CA (US)

(73) Assignee: Ekso Bionics, Inc., Richmond, CA (US)

( * ) Notice: Subject to any disclaimer, the term of this patent is extended or adjusted under 35 U.S.C. 154(b) by 455 days.

(21) Appl. No.: 14/774,536

(22) PCT Filed: Mar. 11, 2014

(86) PCT No.: PCT/US2014/023524
§ 371 (c)(1),
(2) Date: Sep. 10, 2015

(87) PCT Pub. No.: WO2014/164804
PCT Pub. Date: Oct. 9, 2014

(65) Prior Publication Data
US 2016/0038371 A1 Feb. 11, 2016

Related U.S. Application Data

(60) Provisional application No. 61/779,633, filed on Mar. 13, 2013.

(51) Int. Cl.
*A61H 3/02* (2006.01)
*A61H 3/00* (2006.01)
(Continued)

(52) U.S. Cl.
CPC .................. *A61H 3/02* (2013.01); *A61F 5/01* (2013.01); *A61H 3/00* (2013.01); *A61H 3/0244* (2013.01);
(Continued)

(58) Field of Classification Search
CPC .......... A61H 3/02; A61H 3/00; A61H 3/0244; A61H 1/0255; A61H 2003/0205;
(Continued)

(56) References Cited

U.S. PATENT DOCUMENTS 2,920,370 A * 1/1960 Granville ................ E05C 19/14
24/271
3,986,502 A 10/1976 Gilson
(Continued)

FOREIGN PATENT DOCUMENTS

CN 102440891 5/2012
CN 102440891 A * 5/2012
(Continued)

*Primary Examiner* — Ophelia A Hawthorne
(74) *Attorney, Agent, or Firm* — Diederiks & Whitelaw, PLC

(57) ABSTRACT

A gait orthotic system includes a balance aid and a gait orthotic device. The gait orthotic device has a rigid attachment mechanism configured to securely and releasably couple the balance aid to the gait orthotic device. When the balance aid is coupled to the gait orthotic device, the gait orthotic device is supported in a standing position so that a user of the gait orthotic device is able to use his/her hands freely. When the balance aid is not coupled to the gait orthotic device, the user is able to use the balance aid for locomotion. In certain embodiments, the balance aid is a forearm crutch, a walker or a cane, while the rigid attachment mechanism is a clamp with an over-center latch.

19 Claims, 5 Drawing Sheets

(51) Int. Cl.
*A61F 5/01* (2006.01)
*A61H 1/02* (2006.01)

(52) U.S. Cl.
CPC .... *A61H 1/0255* (2013.01); *A61H 2003/0205* (2013.01); *A61H 2201/164* (2013.01); *A61H 2201/165* (2013.01); *A61H 2201/1623* (2013.01)

(58) Field of Classification Search
CPC ...... A61H 2201/1623; A61H 2201/164; A61H 2201/165; A61F 5/01
See application file for complete search history.

(56) References Cited

U.S. PATENT DOCUMENTS

| | | | |
|---|---|---|---|
| 4,697,808 A | 10/1987 | Larson et al. | |
| 4,809,804 A | 3/1989 | Houston et al. | |
| 5,040,556 A | 8/1991 | Raines | |
| 5,300,016 A | 4/1994 | Marlatt | |
| 5,467,793 A | 11/1995 | Hart | |
| 5,942,985 A * | 8/1999 | Chin | G07C 9/00309 340/10.33 |
| 6,206,018 B1 | 3/2001 | Daniels, Jr. | |
| 7,303,537 B1 | 12/2007 | Snyder et al. | |
| 7,544,172 B2 | 6/2009 | Santos-Munne et al. | |
| 8,257,291 B2 | 9/2012 | Kazerooni et al. | |
| 8,453,663 B2 | 6/2013 | Zordan et al. | |
| 2004/0011392 A1 | 1/2004 | Maulden et al. | |
| 2010/0051371 A1* | 3/2010 | Kaufman | G05D 1/0891 180/170 |
| 2011/0201978 A1 | 8/2011 | Jeon et al. | |
| 2011/0266323 A1* | 11/2011 | Kazerooni | B25J 9/0006 224/575 |
| 2011/0319801 A1 | 12/2011 | Ital et al. | |
| 2013/0138031 A1 | 5/2013 | Bergmann | |

FOREIGN PATENT DOCUMENTS

| | | |
|---|---|---|
| DE | 10128382 | 12/2002 |
| DE | 10361146 | 7/2004 |
| GB | 2166048 | 4/1986 |
| WO | WO 2006074029 | 7/2006 |
| WO | WO 2012/027336 | 3/2012 |
| WO | WO 2012037555 | 3/2012 |

* cited by examiner

GAIT ORTHOTIC SYSTEM AND METHOD FOR ACHIEVING HANDS-FREE STABILITY

CROSS REFERENCE TO RELATED APPLICATIONS

The present application represents a National Stage application of PCT/US2014/023524 entitled "Gait Orthotic System and Method for Achieving Hands-Free Stability" filed Mar. 11, 2014, pending, which claims the benefit of U.S. Provisional Patent Application Ser. No. 61/779,633 entitled "Achieving Hands Free Stability in Gait Orthotic Devices" filed Mar. 13, 2013. The entire content of these applications is incorporated herein by reference.

BACKGROUND OF THE INVENTION

The present invention pertains to gait orthotic devices and, more particularly, to gait orthotic devices that enable users thereof to make free use of their hands.

Powered and unpowered gait orthotic devices have been developed that allow people with mobility disorders to walk and perform tasks that are difficult to accomplish from a wheelchair. A user of a gait orthotic device typically improves stability by expanding his/her support base with a balance aid, such as a forearm crutches (also known as Lofstrand crutches), a walker or a cane. In most cases, the user holds on to the balance aid with his/her hands and arms even while standing for prolonged periods. Thus, a user's hands are not free when utilizing these devices. For locomotion, this is deemed acceptable but, for prolonged periods of standing still, it would be beneficial if the user's hands were free for other purposes. With the above in mind, there is considered to be a need in the art for a gait orthotic device that eliminates or mitigates these problems by allowing a user to freely use his/her hands when standing.

SUMMARY OF THE INVENTION

In general, the present invention describes how to expand the support base of the user and the user's gait orthotic device, and thus increase stability, while also freeing the user's hands for other purposes. With his/her hands free, the user is able to, for example, lift and move objects of reasonable weight with appropriate floor friction and muscular function. In particular, the present invention is directed to a gait orthotic system including a balance aid and a gait orthotic device. The gait orthotic device has a rigid attachment mechanism configured to securely and releasably couple the balance aid to the gait orthotic device. When the balance aid is coupled to the gait orthotic device, the gait orthotic device is supported in a standing position so that a user of the gait orthotic device is able to use his/her hands freely. When the balance aid is not coupled to the gait orthotic device, the user is able to use the balance aid for locomotion. Preferably, the balance aid is a forearm crutch, a walker or a cane, while the rigid attachment mechanism is a clamp with an over-center latch.

In a preferred embodiment, the rigid attachment mechanism is movable between first and second positions. In the first position, the rigid attachment mechanism is configured to retain the balance aid in a first orientation to support the gait orthotic device from in front of the user. In the second position, the rigid attachment mechanism is configured to retain the balance aid in a second orientation to support the gait orthotic device from behind the user. In a further preferred embodiment, the gait orthotic device has a second, lower rigid attachment mechanism movable between first and second positions. In the first position, the lower rigid attachment mechanism is configured to retain the balance aid in the first orientation while, in the second position, the lower rigid attachment mechanism is configured to retain the balance aid in the second orientation. In an alternative embodiment, two lower rigid attachment mechanisms are employed, with one corresponding to the first orientation and the other corresponding to the second orientation.

In another preferred embodiment, the gait orthotic device system includes a controller, which is configured to release the balance aid from the rigid attachment mechanism upon receiving a signal. Additionally, the gait orthotic system preferably includes a sensor that is configured to detect whether the balance aid is coupled to the rigid attachment mechanism and also an orientation of the balance aid. In certain configurations, a sensor is configured to detect a force applied to the balance aid, a force applied to the rigid attachment mechanism and an orientation of the balance aid, and a controller is configured to maximize the stability of the gait orthotic device based on this information.

Additional objects, features and advantages of the invention will become more readily apparent from the following detailed description of preferred embodiments thereof when taken in conjunction with the drawings wherein like reference numerals refer to common parts in the several views.

DETAILED DESCRIPTION OF PREFERRED EMBODIMENTS

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

In general, the following embodiments expand a user's support base by connecting a balance aid rigidly to a gait orthotic device while securing a ground contacting end of the balance aid as far away from the feet of the device as practically possible in the sagittal and frontal planes.

Expanding the support base provides greater resistance to overturning, i.e., falling, and increases stability. To provide reliable system stability, the connections need enough strength and stiffness to provide static equilibrium. If there is any relative motion at the connections, it should not be large enough to erode user confidence in the device.

Figure 1:
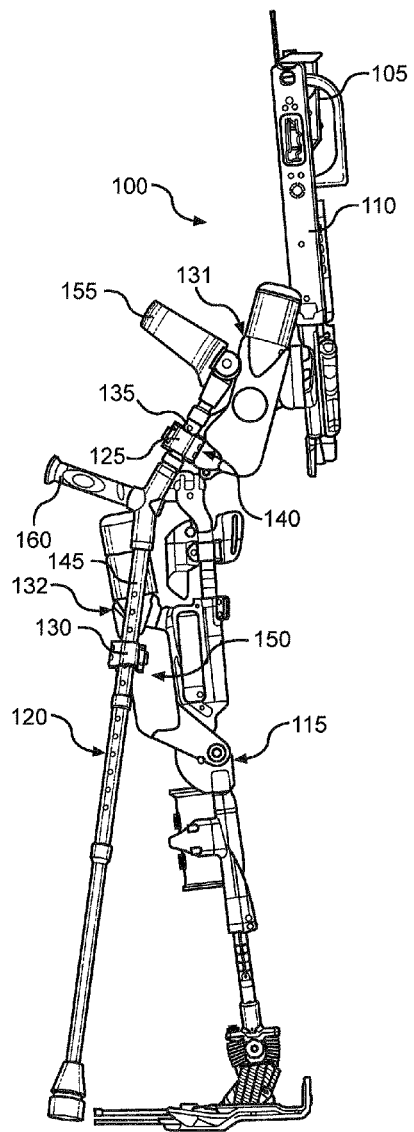
FIG. 1 is a perspective view of a gait orthotic device with a balance aid in a first orientation.
Figure 2:
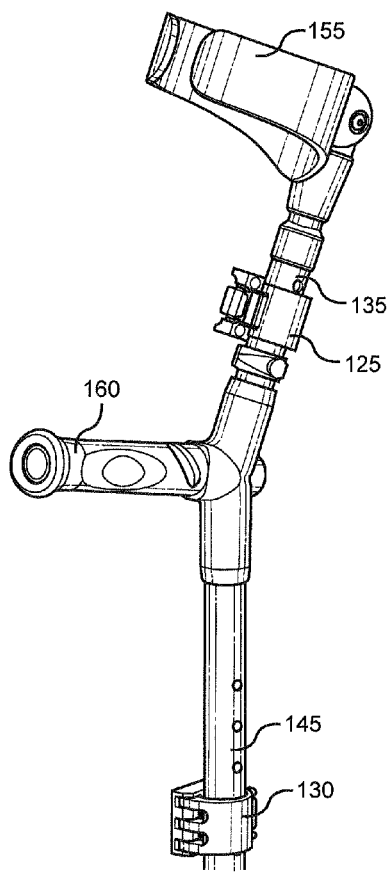
FIG. 2 is another perspective view of the gait orthotic device and balance aid in the first orientation.

With reference now to FIGS. 1 and 2, there is shown a gait orthotic device 100 in accordance with the present invention. Specifically, device 100 is a powered orthotic device in the form of an exoskeleton. However, the present invention is not limited to such devices. Device 100 includes a control system or controller 105, a torso 110, a left leg 115 and a right leg, which is not visible in this view. A left forearm crutch 120 is coupled to device 100 by an upper clamp 125 and a lower clamp 130. At this point, it should be understood that a right forearm crutch (not shown for clarity of the drawing) is also coupled to device 100 by clamps. Both left leg 115 and right leg have actuated knees and hips. In particular, left leg has a hip actuator 131 and a knee actuator 132 and right leg has corresponding hip and knee actuators, which are not visible in these drawings. A user wears device 100 with torso 110 coupled to the user's torso, left leg 115 coupled to the user's left leg and right leg coupled to the user's right leg. Controller 105 controls the motion of device 100 through the hip and knee actuators of each leg, e.g., actuators 131, 132, based on various signals received from sensors (not shown), as known in the art, so that the user is able to walk.

Figures 3, 4:
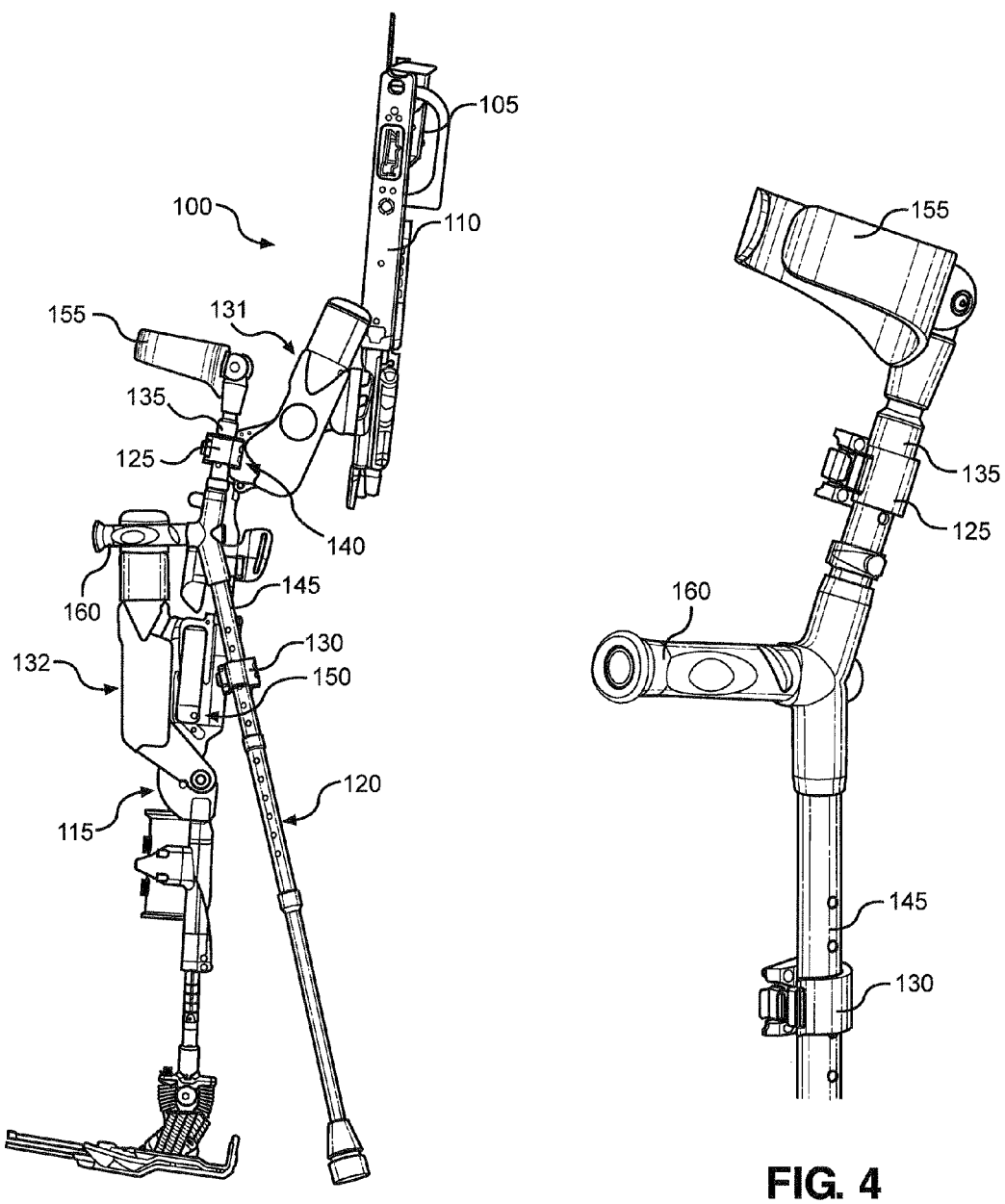
FIG. 3 is a perspective view of the gait orthotic device with the balance aid in a second orientation.
FIG. 4 is another perspective view of the gait orthotic device and balance aid in the second orientation.
Figure 5:
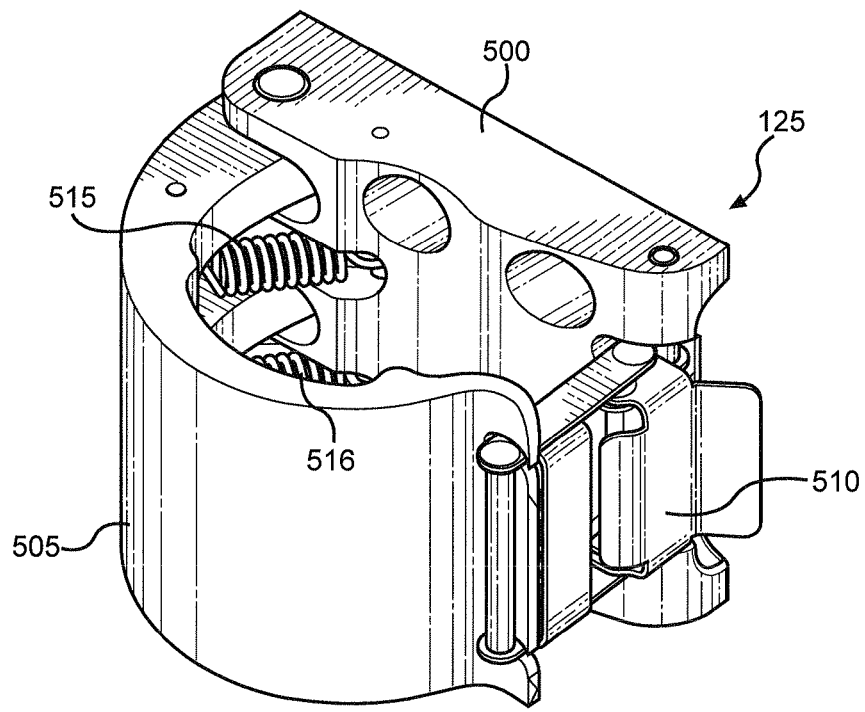
FIG. 5 is a perspective view of a clamp mechanism for use with the present invention.
Figure 6:
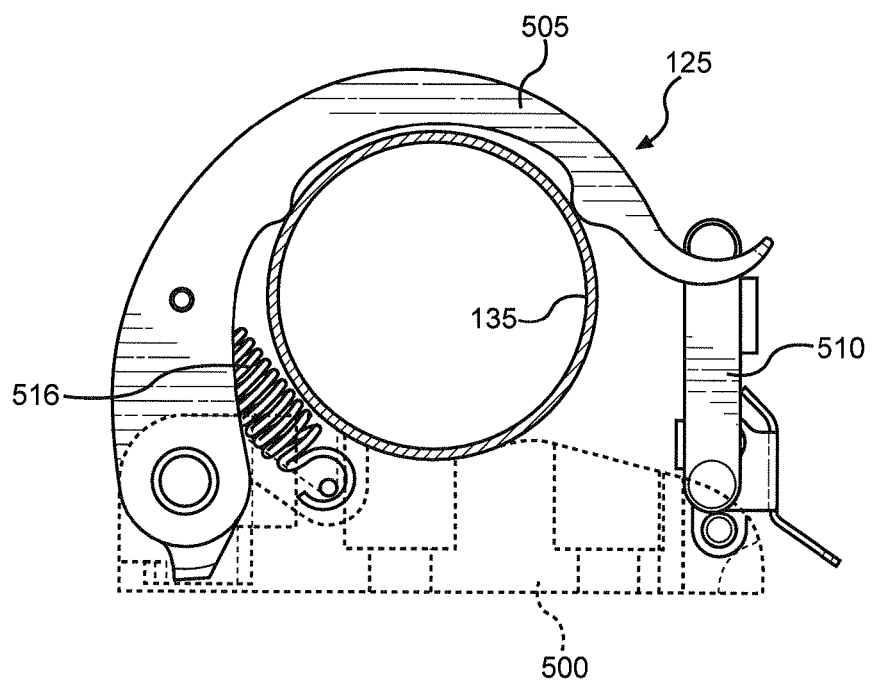
FIG. 6 is an end view of the clamp mechanism of FIG. 5 in a closed position.
Figure 7:
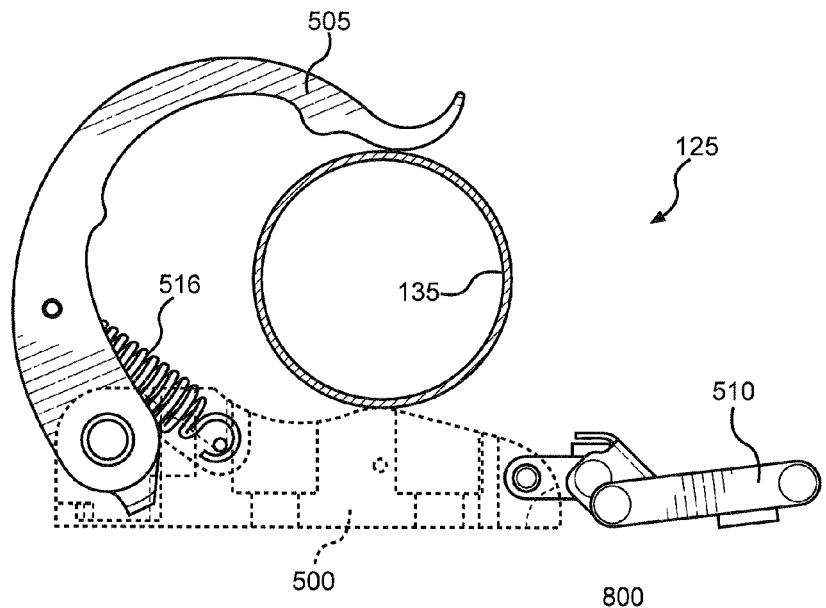
FIG. 7 is an end view of the clamp mechanism in a partially open position.
Figure 8:
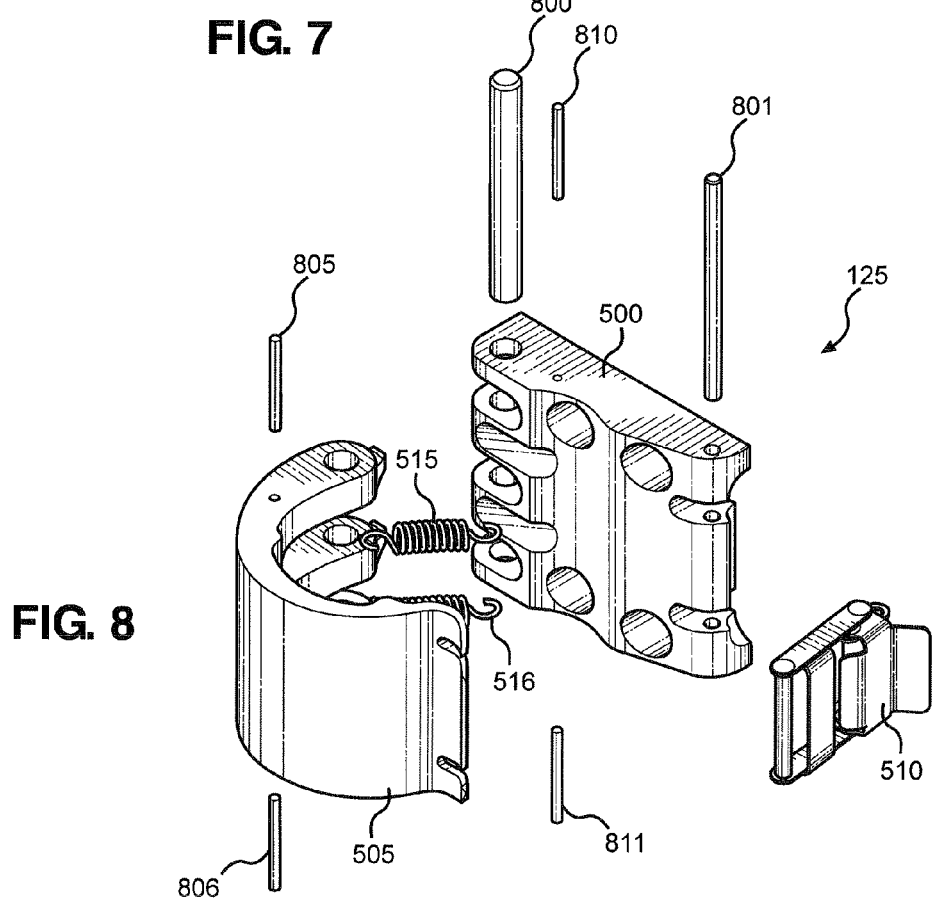
FIG. 8 is an exploded perspective view of the clamp mechanism.

FIGS. 1 and 2 show crutch 120 securely coupled to device 100 in the preferred configuration for a front-supported orientation. Upper clamp 125 is coupled to an upper shaft 135 of crutch 120 and centered about an axis parallel to a hip joint 140. Such a location is advantageous because device 100 can be supported while still allowing the angle of torso 110 to change for maximal stability. In some embodiments, however, it is desirable to locate upper clamp 125 above hip joint 140 so that, while clamps 125, 130 are locked, hip joint 140 is locked and device 100 consumes no power to hold a position about hip joint 140. Lower clamp 130 is coupled to a lower crutch shaft 145 and a thigh portion 150. FIGS. 3 and 4 show crutch 120 securely coupled to device 100 in the preferred configuration for the rear-supported orientation. As above, upper clamp 125 is coupled to upper shaft 135 of crutch 120 and centered about an axis parallel to hip joint 140. Lower clamp 130 is coupled to lower crutch shaft 145 and a different portion of thigh portion 150.

In order to allow device 100 to function in both the front- and rear-supported orientations, upper clamp 125 is preferably coupled to device 100 in such a manner that it can rotate about an axis parallel to hip joint 140 between two prescribed angular orientations that are selectable by a user (shown in FIGS. 1 and 3 respectively). Similarly, clamp 130 is provided at discrete locations with one being used in each orientation. Alternatively, clamp 130 can be configured to pivot between the two positions such that a single clamp can be used in both orientations, which reduces the mass of device 100. When adjusting the position of lower clamp 130, it preferably rotates freely enough to enable easy adjustment, but has enough resistance so that gravitational forces do not cause it to change position. Ideally, a spring-loaded detent device (not shown) can be employed to provide additional resistance to rotation at three prescribed rotational orientations that create additional resistance the user can feel while adjusting. The additional resistance at the prescribed rotational orientations indicates the ideal positions for front-supported orientation, the rear-supported orientation and a centrally oriented position for stowage when not being used for crutch attachment. However, in other embodiments, upper clamp 125 does not rotate and only a single, non-pivotal lower clamp 130 is provided such that device 100 only functions in either the front- or rear-supported orientation.

Although reference is made to clamps, it should be readily apparent that any rigid attachment mechanism known in the art can be used. In some embodiments, the connections can be purely mechanical clamps or latches while, in other embodiments, the connections can be electrically controlled by a device such as a brake, solenoid, motor or electromagnet operated by controller 105. The simplest embodiment is a "C"-shaped flexible member that expands around a shaft of crutch 120 much the way a forearm collar 155 of crutch 120 functions.

For maximum safety and convenience, it is preferable that the user can maneuver crutch 120 from its free state into and out of clamps 125, 130 while the user is holding a handle 160 of crutch 120 the way it is normally used for balance. Thus, it is desirable that the user be able to release clamps 125, 130 while holding handle 160. In some embodiments, this is achieved with a mechanical release trigger actuated by one or more of the user's fingers or by a twisting motion of crutch 120. In other embodiments, where the connection is actuated, the user can signal controller 105 to release crutch 120. The signal can be a voice command, surrogate muscle contraction or any other method of providing input to device 100. In some embodiments, controller 105 frees clamps 125 when crutch 120 crosses a specified degree of freedom. FIG. 2 shows a preferred configuration of clamps 125, 130 for the front-supported orientation, while FIG. 4 shows a preferred configuration of clamps 125, 130 for the rear-supported orientation. For safety and confidence, both upper clamp 125 and lower clamp 130 should not accidently be released during intended hands-free use. One way to ensure this desired function is to provide clamps 125, 130 with a mechanism that maintains the connection rigidity, such as an over-center latch. However, there are many solutions well understood in the art that can achieve this functionality.

With reference now to FIGS. 5 through 8, a more detailed view of clamp 125 is provided, though it should be understood that clamp 130 can be constructed in an analogous manner. Clamp 125 includes an attachment portion 500, for coupling to device 100, and a pivotal portion 505, which together define an opening (not labeled) for receiving a portion of crutch 120, such as upper shaft 135. An over-center latch 510 is provided to secure clamp 125 in a latched position (shown in FIGS. 5 and 6). Additionally, the force of springs 515, 516 tends to keep pivotal portion 505 near the latched position. When latch 510 is released, pivotal portion 505 can be moved, against the action of spring 515, 516, to the position shown in FIG. 7 such that upper shaft 135 can be removed from or inserted into clamp 125. Pins 800, 801 are provided to pivotally couple pivotal portion 505 and latch 510, respectively, to attachment portion 500. Additionally, pins 805, 806 and pins 810, 811 are provided to couple springs 515, 516 to pivotal portion 505 and attachment portion 500, respectively. As a result, clamp 125 simply and securely retains crutch 120 when desired by the user, while also permitting the user to quickly and easily release crutch 120 from clamp 125.

Although the balance aid references above takes the form of crutches, other balancing aids could be employed. In fact, a walker provides the simplest embodiment of the invention because, unlike crutches, it is inherently stable, and thus does not require a user to balance it. To provide stability, a walker is oriented to the front, rear or either side of device 100 using any of a wide variety of rigid connections. The preferred walker orientation depends on the desired hands-free activity. In a preferred embodiment, device 100 allows both front and rear rigid connections with the same components. Still, forearm crutches, such as crutch 120, are a more versatile balance aid than a walker, but require more skill to use because they are not inherently stable. Such crutches allow for a wide variety of orientations and rigid connections to device 100, as discussed above. In the frontal plane, the ends of the crutches contact the ground to the outside of the device's feet. In the sagittal plane, the crutch ends are held in place in front of or behind the system feet with rigid connections. The placement of the crutch ends provides different advantages and disadvantages for the user. If the crutches are supporting device 100 from in front of the device's feet, device 100 will lean forward of vertical to maximize stability. If the crutches are supporting device 100 from behind the device's feet, the device 100 will lean backwards from vertical to maximize stability. In a preferred embodiment, the user has a choice of whether to support device 100 from the front or the rear and thereby maximize stability in either orientation.

Figure 9:
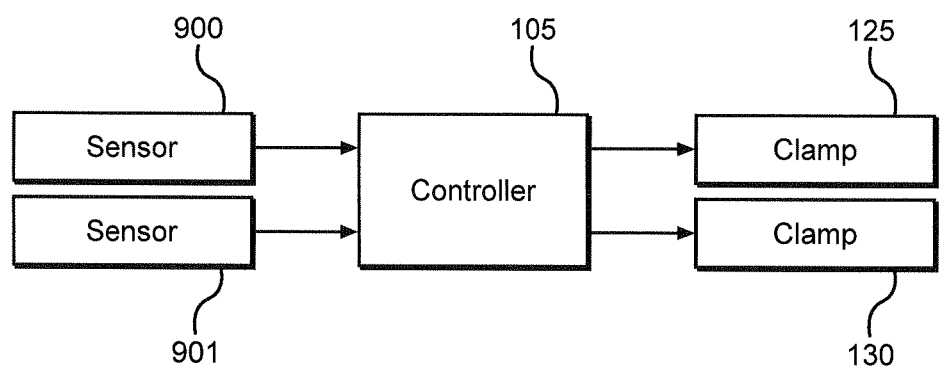
FIG. 9 schematically illustrates a control system employed in connection with the invention.

Powered exoskeletons, such as device 100, are one form of gait orthotic device that can provide maximal stability in either front or rear support orientations, e.g., crutch orientations. To accomplish this, device controller 105 is informed of the presence of crutches and their direction of support (i.e., front or rear orientation), and then adjusts torso, thigh and shank positions accordingly. In some embodiments, as schematically illustrated in FIG. 9, there are electronic or mechanical sensors or switches 900, 901 at or near the crutch connections that indicate to controller 105 one or more of the following: the crutches are present in the connections; the connections are rigidly set; and the location and orientation of the crutches relative to the connections. In these embodiments, controller 105 can automatically reposition device 100 to take advantage of the additional ground support and the expanded support base. In some embodiments, the crutches themselves contain the presence-, position- and orientation-detecting sensors. As such, controller 105 can employ safety checks prior to repositioning device 100 to ensure the crutches will provide rigid support.

In addition, sensors 900, 901 can be used on the crutches or device 100 to detect the forces applied to the crutches or the connections and report this information to controller 105. These embodiments allow controller 105 to further adjust device 100 to maximize stability. In the most sophisticated embodiments, controller 105 can measure the orientation of device 100 in space and the load distribution of device 100 on the ground, and controller 105 can even estimate the total center of pressure and center of mass of the system. Crutch position- and force-sensing also allow the controller to adjust device 100 as objects are lifted up and moved by the user. In addition, safety alarms can be triggered if the user exceeds the limits of their support base. Of course, it should be readily apparent that it is also possible for the user to simply tell controller 105, through a user interface (not shown), when the crutches are connected. In some embodiments, it is desirable for controller 105 to know that the crutches are present because the crutches cross a powered degree of freedom, and device 100 should not move through this degree of freedom because doing so can damage clamps 125, 130 or cause instability.

When a user loads crutch-supported device 100 with over-turning moments, there is some lean angle developed away from vertical from a variety of compliant sources. The amount of change in lean angle is inversely related to the rigidity of the connections between device 100 and crutch 120. It is therefore preferable that these connections not be attached to compliant components, such as padded crutch handle 160. While connecting to crutch handle 160 might otherwise provide a good solution, the preferred embodiments attach to rigid, metal aspects of the crutches. Additionally, a primary goal of the invention is to enable a user to use his/her hands for purposes other than balance. To achieve this goal, it is also important that free motion of the hands and arms are obstructed as little as possible when the balance aid is connected to device 100. For forearm crutches, the portion of the crutch above handle 160 can obstruct free motion of the arms in many orientations that would otherwise provide stability. Numerous possible orientations were evaluated to determine the preferred orientations for front and rear device support.

Based on the above, it should be readily apparent that the present invention provides for a gait orthotic device that allows a user to freely use his/her hands when standing. Although described with reference to preferred embodiments, it should be readily understood that various changes or modifications could be made to the invention without departing from the spirit thereof. For example, the present invention is usable in a broad range of gait orthotic devices, both powered and unpowered. In general, the invention is only intended to be limited by the scope of the following claims.

The invention claimed is:

1. A gait orthotic system comprising:
   a balance aid; and
   a gait orthotic device including:
      a rigid attachment mechanism configured to securely and releasably couple the balance aid to the gait orthotic device, whereby a user of the gait orthotic device is able to use his/her hands freely when the balance aid is coupled to the gait orthotic device and the user is able to use the balance aid for locomotion when the balance aid is not coupled to the gait orthotic device, wherein the rigid attachment mechanism is configured to prevent relative movement between the balance aid and the gait orthotic device at the rigid attachment mechanism when the balance aid is coupled to the gait orthotic device.

2. The gait orthotic system of claim 1, wherein: if the rigid attachment mechanism is movable between a first position and a second position;
   the rigid attachment mechanism is configured to retain the balance aid in a first orientation, to support the gait orthotic device from a first direction, when the rigid attachment mechanism is in the first position; and
   the rigid attachment mechanism is configured to retain the balance aid in a second orientation, to support the gait orthotic device from a second direction, when the rigid attachment mechanism is in the second position.

3. The gait orthotic system of claim 2, wherein:
   the balance aid supports the gait orthotic device from in front of the user when the rigid attachment mechanism is in the first position; and
   the balance aid supports the gait orthotic device from behind the user when the rigid attachment mechanism is in the second position.

4. The gait orthotic system of claim 2, wherein the rigid attachment mechanism constitutes an upper rigid attachment mechanism and the gait orthotic device further includes a lower rigid attachment mechanism that is movable between a first position and a second position;

the lower rigid attachment mechanism is configured to retain the balance aid in the first orientation when the lower rigid attachment mechanism is in the first position; and the lower rigid attachment mechanism is configured to retain the balance aid in the second orientation when the lower rigid attachment mechanism is in the second position.

5. The gait orthotic system of claim 2, wherein the rigid attachment mechanism constitutes an upper rigid attachment mechanism and the gait orthotic device further includes a first lower rigid attachment mechanism and a second lower rigid attachment mechanism, and further wherein:

the first lower rigid attachment mechanism is configured to retain the balance aid in the first orientation; and the second lower rigid attachment mechanism is configured to retain the balance aid in the second orientation.

6. The gait orthotic system of claim 1, wherein the gait orthotic device further includes a controller, the controller being configured to release the balance aid from the rigid attachment mechanism upon receiving a signal.

7. The gait orthotic system of claim 1, wherein the gait orthotic device further includes a sensor, the sensor being configured to detect:

whether the balance aid is coupled to the rigid attachment mechanism; or an orientation of the balance aid.

8. The gait orthotic system of claim 1, wherein the gait orthotic device further includes:

a sensor configured to detect:
  a force applied to the balance aid or to the rigid attachment mechanism; or
  an orientation of the balance aid; and a controller configured to maximize stability for the gait orthotic device based on:
  the force applied to the balance aid or to the rigid attachment mechanism; or
  the orientation of the balance aid.

9. The gait orthotic system of claim 1, wherein the balance aid is a forearm crutch, a walker or a cane.

10. The gait orthotic system of claim 1, wherein the rigid attachment mechanism is a clamp with an over-center latch.

11. A method for achieving hands-free stability for a user of a gait orthotic device comprising:

securely and releasably coupling a balance aid to the gait orthotic device using a rigid attachment mechanism, wherein securely and releasably coupling the balance aid to the gait orthotic device includes preventing relative movement between the balance aid and the gait orthotic device at the rigid attachment mechanism;

supporting the gait orthotic device in a standing position with the balance aid when the balance aid is coupled to the gait orthotic device; and allowing a user of the gait orthotic device to use the balance aid for locomotion when the balance aid is not coupled to the gait orthotic device.

12. The method of claim 11, further comprising:

moving the rigid attachment mechanism to a first position to retain the balance aid in a first orientation and support the gait orthotic device from a first direction; and moving the rigid attachment mechanism to a second position to retain the balance aid in a second orientation and support the gait orthotic device from a second direction.

13. The method of claim 12, wherein supporting the gait orthotic device from the first direction includes supporting the gait orthotic device from in front of the user and supporting the gait orthotic device from the second direction including supporting the gait orthotic device from behind the user.

14. The method of claim 12, wherein the rigid attachment mechanism constitutes an upper rigid attachment mechanism and the gait orthotic device further includes a lower rigid attachment mechanism, said method further comprising:

moving the lower rigid attachment mechanism to a first position to retain the balance aid in the first orientation; and moving the lower rigid attachment mechanism to a second position to retain the balance aid in the second orientation.

15. The method of claim 12, wherein the rigid attachment mechanism constitutes an upper rigid attachment mechanism and the gait orthotic device further includes a first lower rigid attachment mechanism and a second lower rigid attachment mechanism, said method further comprising:

retaining the balance aid in the first orientation using the first lower rigid attachment mechanism; and retaining the balance aid in the second orientation using the second lower rigid attachment mechanism.

16. The method of claim 11, further comprising:
sending a signal to a controller to release the balance aid from the rigid attachment mechanism.

17. The method of claim 11, further comprising:
detecting, with a sensor:
  whether the balance aid is coupled to the rigid attachment mechanism; or
  an orientation of the balance aid.

18. The method of claim 11, further comprising:
detecting, with a sensor:
  a force applied to the balance aid or to the rigid attachment mechanism; or
  an orientation of the balance aid; and
maximizing stability, with a controller, based on:
  the force applied to the balance aid or to the rigid attachment mechanism; or
  the orientation of the balance aid.

19. The method of claim 11, wherein securely and releasably coupling the balance aid to the gait orthotic device using the rigid attachment mechanism includes securely and releasably coupling a forearm crutch, a walker or a cane to the gait orthotic device using a clamp with an over-center latch.

* * * * *